United States Patent
Chassaing et al.

(10) Patent No.: US 12,281,104 B2
(45) Date of Patent: Apr. 22, 2025

(54) PROCESS FOR THE PRODUCTION OF ETHYL 3-AMINO-1-[(3R,4S)-4-CYANOTETRA-HYDROPYRAN-3-YL]PYRAZOLE-4-CARBOXYLATE THROUGH CHIRAL SEPARATION OF A RACEMIC MIXTURE

(71) Applicant: Intervet Inc., Madison, NJ (US)

(72) Inventors: Christophe Pierre Alain Chassaing, Schwabenheim (DE); Karl-Heinz Grimm, Schwabenheim (DE)

(73) Assignee: Intervet Inc., Rahway, NJ (US)

( * ) Notice: Subject to any disclaimer, the term of this patent is extended or adjusted under 35 U.S.C. 154(b) by 792 days.

(21) Appl. No.: 17/606,248

(22) PCT Filed: May 1, 2020

(86) PCT No.: PCT/EP2020/062180
§ 371 (c)(1),
(2) Date: Oct. 25, 2021

(87) PCT Pub. No.: WO2020/221914
PCT Pub. Date: Nov. 5, 2020

(65) Prior Publication Data
US 2022/0204483 A1    Jun. 30, 2022

(30) Foreign Application Priority Data
May 2, 2019   (EP) .................................... 19172248

(51) Int. Cl.
*C07D 405/04*    (2006.01)

(52) U.S. Cl.
CPC ................................. *C07D 405/04* (2013.01)

(58) Field of Classification Search
CPC ..................................................... C07D 405/04
USPC ..................................................... 548/365.7
See application file for complete search history.

(56) References Cited

FOREIGN PATENT DOCUMENTS

| | | |
|---|---|---|
| IN | 202117025506 A | 12/2021 |
| JP | 08231489 A | 9/1996 |
| RU | 2019121667 A | 1/2021 |
| WO | 2013041042 A1 | 3/2013 |
| WO | 2018108969 A1 | 6/2018 |
| WO | 2018111663 A1 | 6/2018 |
| WO | 2020120673 A1 | 6/2020 |

OTHER PUBLICATIONS

Ghanem, A. et al., Enantioselective separation of racemates using Chiralpak IG amylose-based chiral stationary phase under normal standard, nonstandard and reversed phase high performance liquid chromatography, Journal of Chromatography A, 2018, 89-97, 1532.

*Primary Examiner* — Taofiq A Solola
(74) *Attorney, Agent, or Firm* — David J. Kerwick

(57) ABSTRACT

A process for chiral separation of ethyl 3-amino-1-[(3R,4S)-4-cyanotetrahydropyran-3-yl]pyrazole-4-carboxylate (VI) from the racemic mixture of ethyl 3-amino-1-[(3R,4S)-4-cyanotetrahydropyran-3-yl]pyrazole-4-carboxylate and ethyl 3-amino-1-[(3S,4R)-4-cyanotetrahydropyran-3-yl]pyrazole-4-carboxylate (V).

20 Claims, No Drawings

PROCESS FOR THE PRODUCTION OF ETHYL 3-AMINO-1-[(3R,4S)-4-CYANOTETRAHYDROPYRAN-3-YL]PYRAZOLE-4-CARBOXYLATE THROUGH CHIRAL SEPARATION OF A RACEMIC MIXTURE

CROSS-REFERENCE TO RELATED APPLICATIONS

This application is a national stage entry under 35 U.S.C. § 371 of PCT/EP2020/062180 filed May 1, 2020, which claims priority to EP Application Serial No. 19172248.7, filed May 2, 2019; the content of EP19172248.7, is hereby incorporated by reference in its entirety.

BACKGROUND

WO 2018/108969 discloses compounds of formula I which are selective Janus kinase (JAK) inhibitors, and as such are useful for the treatment of JAK-mediated diseases such as atopic dermatitis, arthritis, and cancer. Specifically, 1-[(3R,4S)-4-cyanotetrahydropyran-3-yl]-3-[(2-fluoro-6-methoxy-4-pyridyl)amino]pyrazole-4-carboxamide (I) is disclosed.

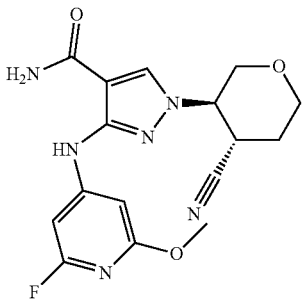

Formula (I)

In the process of preparing the compound of Formula (I), a chiral separation was conducted on a racemic mixture (5) to isolate the key intermediate (6).

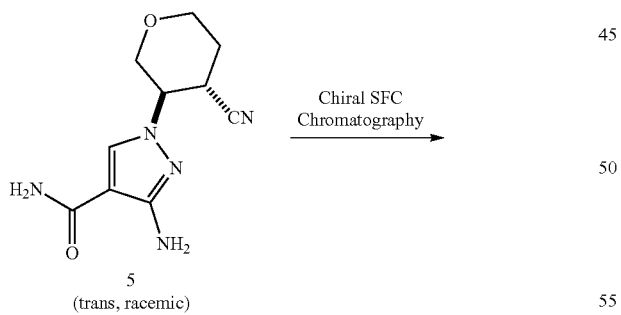

Due to the low solubility of the racemic compound 5 in organic solvents habitually used as eluents for chiral chromatography its separation had to be conducted by supercritical fluid chromatography using a cellulose tris(3,5-dichlorophenylcarbamate) chiral stationary phase (ChiralPak® IC, 10 μM, 300×50 mm) and a mobile phase composed of 45% 2-propanol, 55% $CO_2$; under the following conditions (Flow rate: 220 mL/min; Column temperature: 38° C.).

WO 2013/041042 discloses pyrazole carboxamides as Janus kinase inhibitors that are useful for the treatment of rheumatoid arthritis, asthma, chronic obstructive pulmonary disease (COPD) and cancer. The compounds of this disclosure are of the following formula.

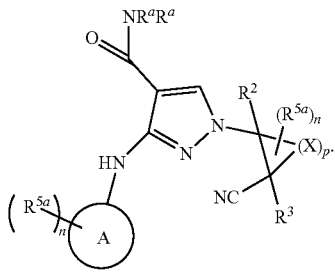

EP18212188 and PCT/CN2018/120821 disclose a process for making 1-[(3R,4S)-4-cyanotetrahydropyran-3-yl]-3-[(2-fluoro-6-methoxy-4-pyridyl)amino]pyrazole-4-carboxamide. This process is summarized in Scheme 1 below.

Scheme 1.
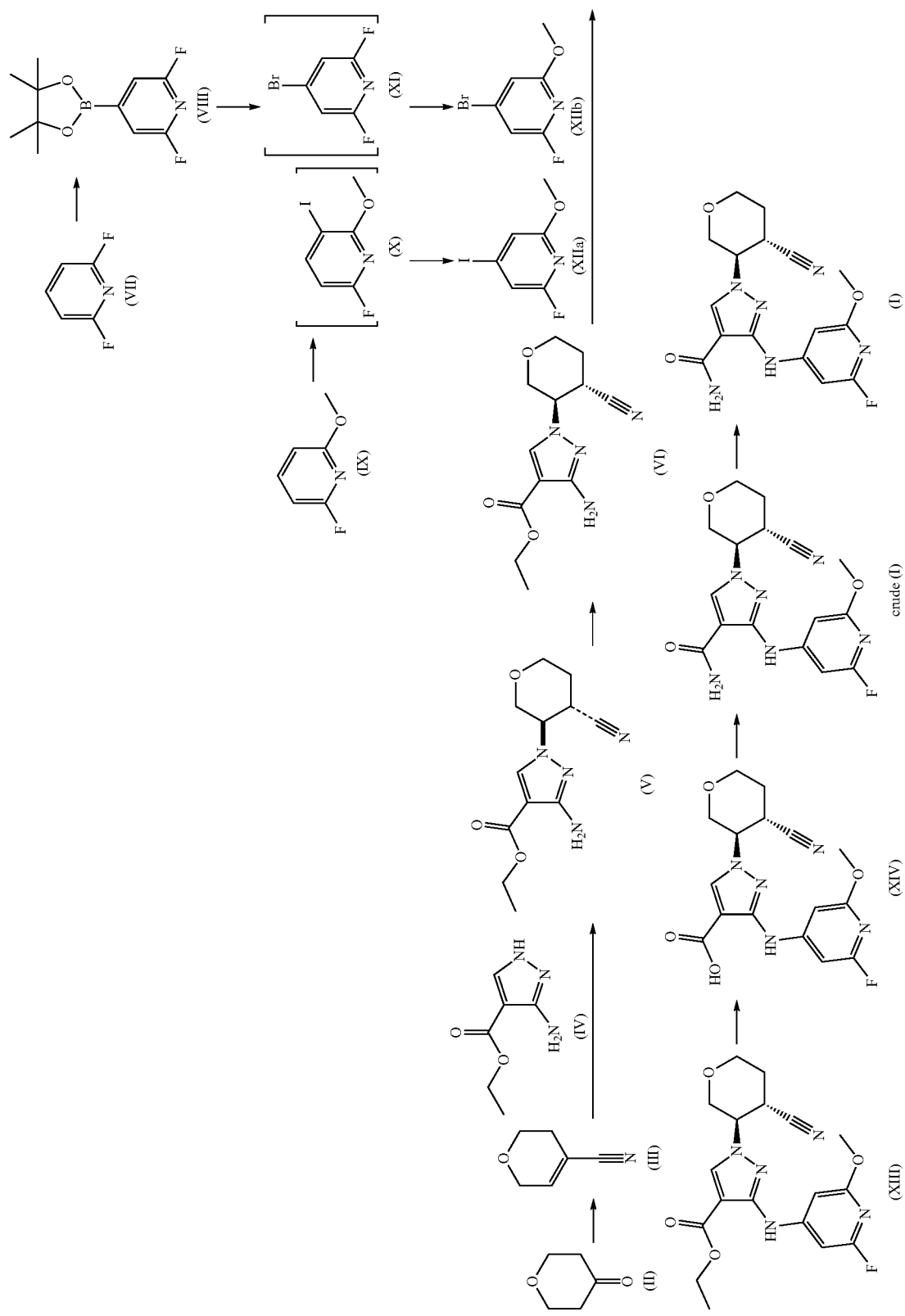

Furthermore, the separation of the racemic mixture of Formula (V) to the enantiomer of Formula (VI) is described as accomplished by HPLC. There is no disclosure of the type of column used.

SUMMARY OF THE INVENTION

Inventors have developed a new and advantageous process for chiral separation of ethyl 3-amino-1-[(3R,4S)-4-cyanotetrahydropyran-3-yl]pyrazole-4-carboxylate (VI) from the racemic mixture of ethyl 3-amino-1-[(3R,4 S)-4-cyanotetrahydropyran-3-yl]pyrazole-4-carboxylate and ethyl 3-amino-1-[(3S,4R)-4-cyanotetrahydropyran-3-yl]pyrazole-4-carboxylate (V).

An embodiment of the invention is a process of producing the compound of Formula VI

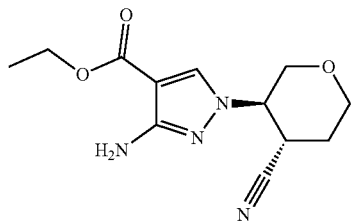

(VI)

comprising separating the enantiomers of the racemic mixture of Formula V

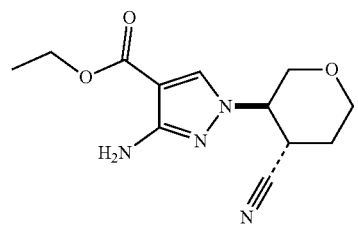

(V)

by chiral chromatography using an eluent and a chiral stationary phase selected from amylose tris(3-chloro-4-methylphenylcarbamate) and amylose tris(3-chloro-5-methylphenylcarbamate).

DETAILED DESCRIPTION

The advantage of the claimed process is the efficient separation of the enantiomers in both high productivity and high selectivity. A process for producing a single enantiomer will normally involve a chiral separation of a racemic compound or an enantiomerically selective reaction. For processes that entail a chiral separation, it is desirable to have this chiral separation as early in the process as possible. This will increase efficiency as the undesired enantiomer is not carried through the subsequent steps. To be truly efficient, the process must be highly selective in separating the two enantiomers.

Furthermore, the process must also have a sufficiently high through put or productivity to produce enough of the desired enantiomer in a reasonable amount of time at affordable costs. In the process disclosed in WO2018/108969 (see above), the chiral separation of a similar intermediate was only able to achieve a productivity of less than 0.5 KKD which in turn determined that the overall process to make the compound of Formula (I) was unacceptable for use in large scale production.

Ethyl 3-amino-1-[(3R,4S)-4-cyanotetrahydropyran-3-yl]pyrazole-4-carboxylate (VI) is a key intermediate in the synthesis of 1-[(3R,4 S)-4-cyanotetrahydropyran-3-yl]-3-[(2-fluoro-6-methoxy-4-pyridyl)amino]pyrazole-4-carboxamide (I). As noted above, EP18212188 and PCT/CN2018/120821 disclose the separation of the racemic mixture of Formula V to enantiomer compound of Formula VI by use of HPLC. See Scheme 2 below Scheme 2

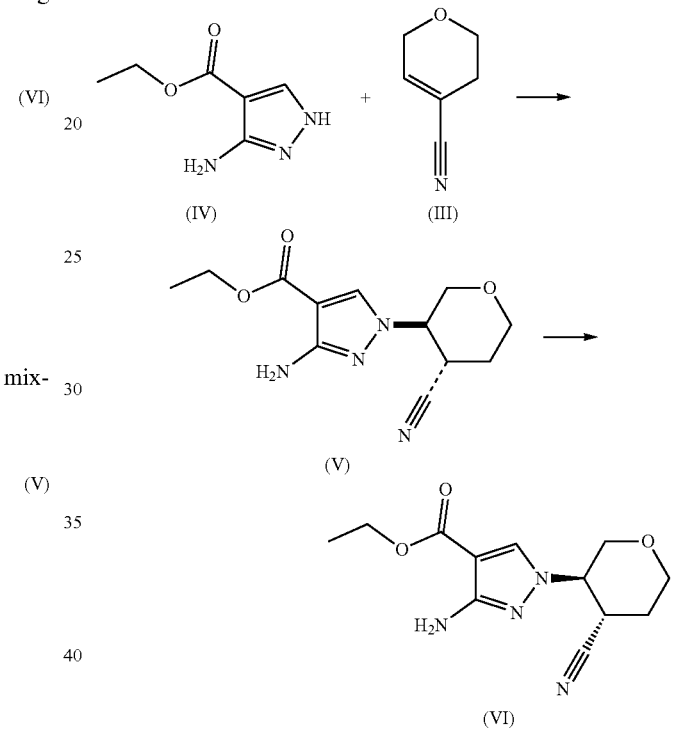

An efficient process for the separation of ethyl 3-amino-1-[(3R,4S)-4-cyanotetrahydropyran-3-yl]pyrazole-4-carboxylate (VI) from the racemic mixture of ethyl 3-amino-1-[(3R,4S)-4-cyanotetrahydropyran-3-yl]pyrazole-4-carboxylate and ethyl 3-amino-1-[(3S,4R)-4-cyanotetrahydropyran-3-yl]pyrazole-4-carboxylate (V) is desired as it allows the remaining steps process described in Scheme 1 above to be conducted on enantiomerically pure material which in turn will result in higher yields for each step and the overall yield. The reaction of Compounds (IV) and (III) initially produces a mixture of four diastereoisomers. In addition to the (3R,4S) and (3S,4R) enantiomers shown as a racemic mixture above (V), the (3R,4R) and the (3S,4S) pair of enantiomers is also produced. However, these later two enantiomers are efficiently separated from (V) by selective recrystallization.

Chiralpak® IG is amylose tris(3-chloro-5-methylphenylcarbamate) immobilized on 3 μm silica gel.

Chiralpak® AZ is amylose tris(3-chloro-4-methylphenylcarbamate) coated on 3 or 5 μm silica gel.

Chiral stationary phases (CSP) are silica-based materials derivatized with polysaccharides that are modified with chiral selectors and which are designed to separate mixtures of enantiomeric compounds. CSP are also known as chiral separation medium.

Coated polysaccharide-based chiral stationary phases are phases in which the polysaccharide is not covalently bonded to the underlying silica.

Immobilized polysaccharide chiral stationary phases are those in which the polysaccharide is covalently linked to the underlying silica.

The efficiency of a chiral separation process can be judged by the degree of separation achieved between the enantiomers of a racemate and the productivity as measured in terms of the mass of racemate processed per the mass of the chiral stationary phase used per 24 hours.

Productivity (KKD) is defined therein as the kg amount of racemate that can be separated per kg of chiral stationary phase (CSP) per day.

The selectivity ($\alpha$) is the ratio of the retention factors of the two UV signals of the two enantiomers as shown in Equation 1. It can be visualized as the distance between the apices of the two UV signals.

$$\alpha = \frac{(T_{E2} - T_0)}{(T_{E1} - T_0)} \quad \text{Equation 1}$$

In which $T_{E2}$ is the retention time of the second eluting enantiomer, $T_{E1}$ is the retention time of the first eluting enantiomer and $T_0$ the time taken by the mobile phase to pass through the column.

Base line separation means process is selective enough so that in the UV chromatogram, the UV signal corresponding to the first component tails off to the base line before the UV signal of the next component begins to show.

Eluent is the mobile phase used to perform the chromatography.

Chiral means the molecule is non-superimposable on its mirror image.

Enantiomer is each of the two non-superimposable images. The Cahn-Ingold-Prelog system is used to designate each enantiomer. The chiral centers of the molecule are assigned a designation of R or S depending upon the configuration of the groups attached to the chiral center. Each group of the four groups attached to an asymmetric carbon (chiral center) is ranked base on a series of priority rules. When the molecule is oriented, so the lowest ranking group is facing away from the viewer, the remaining groups are counted in descending order. If the order proceeds clockwise, the chiral center is designated R. If the order proceeds counterclockwise, the chiral center is designated S. (See March, Advanced Organic Chemistry, $3^{rd}$ Ed. 1985, p 97).

Enantiomeric excess (e.e.) or enantiomeric purity is the degree of enantiomeric purity of a composition expressed as a percentage as indicated in Equation 2

$$e.e.(\%) = \frac{\left(\begin{array}{c}\text{moles of one enantiomer} - \\ \text{moles of the other enantiomer}\end{array}\right)}{\text{(moles of both enantiomers)}} \times 100 \quad \text{Equation 2}$$

The phrase "ethyl 3-amino-1-[(3R,4S)-4-cyanotetrahydropyran-3-yl]pyrazole-4-carboxylate (VI), substantially free of ethyl 3-amino-1-[(3S,4R)-4-cyanotetrahydropyran-3-yl]pyrazole-4-carboxylate" means a composition that comprises at least about 80% e.e. of the compound (VI). Preferably such a composition comprises at least about 90% e.e. of compound (VI), more preferably the composition comprises at least about 95% e.e. of compound (VI) and most preferably, the composition comprises greater than 98% e.e. of compound (VI).

SFC means supercritical fluid chromatography.

SMB means simulated moving bed process.

Racemate or a racemic mixture is one that has equal amounts of left- and right-handed (R and S) enantiomers of a chiral molecule.

An alternative embodiment of the invention is a method of isolating ethyl 3-amino-1-[(3R,4S)-4-cyanotetrahydropyran-3-yl]pyrazole-4-carboxylate (VI), substantially free of ethyl 3-amino-1-[(3S,4R)-4-cyanotetrahydropyran-3-yl] pyrazole-4-carboxylate, said method comprising a) absorbing a racemic mixture of ethyl 3-amino-1-[(3R,4S)-4-cyanotetrahydropyran-3-yl]pyrazole-4-carboxylate and ethyl 3-amino-1-[(3S,4R)-4-cyanotetrahydropyran-3-yl]pyrazole-4-carboxylate (V) onto a chiral separation medium;

b) passing a solvent system through the chiral separation medium in an amount sufficient to elute ethyl 3-amino-1-[4-cyanotetrahydropyran-3-yl]pyrazole-4-carboxylate enantiomers from the separation medium;

c) isolating ethyl 3-amino-1-[(3R,4S)-4-cyanotetrahydropyran-3-yl]pyrazole-4-carboxylate (VI), substantially free of ethyl 3-amino-1-[(3S,4R)-4-cyanotetrahydropyran-3-yl]pyrazole-4-carboxylate;

wherein said chiral separation medium is amylose tris(3-chloro-5-methylphenylcarbamate) immobilized on silica gel or amylose tris(3-chloro-4-methylphenylcarbamate) coated on silica gel.

In another embodiment of the invention, the chiral stationary phase is selected from amylose tris(3-chloro-4-methylphenylcarbamate), amylose tris(5-chloro-2-methylphenylcarbamate), amylose tris(3,5-dimethylphenylcarbamate) and amylose tris(3-chloro-5-methylphenylcarbamate).

In an embodiment, the chiral stationary phase is coated or immobilized on silica gel.

In another embodiment of the invention, the chiral stationary phase is amylose tris(3-chloro-5-methylphenylcarbamate) immobilized on silica gel.

In another embodiment of the invention, the column is amylose tris(3-chloro-4-methylphenylcarbamate) coated on silica gel.

In another embodiment of the invention, the eluent is acetonitrile. In another embodiment of the invention, the productivity of the process is greater than 2.0 KKD.

In another embodiment of the invention, the productivity of the process is in the range of about 2.0 to about 6.0 KKD, preferably about 3.0 to about 5.0 KKD.

In another embodiment of the invention, the selectivity of the process is the range of about 1.0 to about 4.0, preferably about 1.5 to about 3.5.

In another embodiment of the invention, the temperature is between about 20° C. to about 40° C., preferably between about 25° C. to about 35° C.

In another embodiment of the invention, the concentration of the racemate (V) is about 100 g/L to about 300 g/L, preferably about 200 g/L.

EXAMPLES

Example 1 Solubility of Compound (V) in Organic Solvents

The solubility of Compound (V) in water and in a set of organic solvents was determined. The results are shown in Table 1.

| Concentration in pure solvents given in g/L | | | | | |
|---|---|---|---|---|---|
| Water | EtOH | MeOH | iPrOH | Acetonitrile | Iso-Hexane |
| <5 | 10 | <50 | <5 | >200 | 0 |

It was observed that Compound (V) is surprisingly highly soluble in acetonitrile which is one of the solvents of choice for performing chromatographic separations.

TABLE 2

| Stationary Phase | See Table 2 |
|---|---|
| Column dimensions | 4.6 × 250 nm |

TABLE 2-continued

| (inside diameter × length) | |
|---|---|
| Mobile phase | Acetonitrile |
| Flow rate | 1 mL/min |
| UV detection, wave length λ | 220 nm |
| Column temperature | 25° C. |
| Sample temperature | Room temperature |
| Sample diluent | Acetonitrile |
| Sample concentration | 2 g/L |

TABLE 3

| Type of stationary phase | Chiral selector | Particle size (μm) | Corresponding illustrative example | Some separation achieved | Selectivity (α) | Baseline resolution |
|---|---|---|---|---|---|---|
| Immobilized | amylose tris(3,5-dimethylphenylcarbamate) | 20 | Chiralpak ® IA | No | n.a. | n.a. |
| Immobilized | cellulose tris(3,5-dimethylphenylcarbamate) | 20 | Chiralpak ® OD-I | No | n.a. | n.a. |
| Immobilized | amylose tris(3,5-dichlorophenylcarbamate) | 20 | Chiralpak ® IE | Yes | 1.2 | No |
| Immobilized | cellulose tris(3,5-dichlorophenylcarbamate) | 20 | Chiralpak ® IC | Yes | 1.2 | No |
| Immobilized | amylose tris(3-chlorophenylcarbamate) | 20 | Chiralpak ® ID | Yes | 1.3 | No |
| Immobilized | amylose tris(3-chloro-4-methylphenylcarbamate) | 20 | Chiralpak ® IF | Yes | 1.5 | Almost |
| Immobilized | amylose tris(3-chloro-5-methylphenylcarbamate) | 20 | Chiralpak® IG | Yes | 1.7 | Yes |
| Coated | cellulose tris(3-chloro-4-methylphenylcarbamate) | 20 | Chiralcel ® OZ | No | n.a. | n.a. |
| Coated | cellulose tricinnamate | 20 | Chiralcel ® OK | No | n.a. | n.a. |
| Coated | amylose tris [(S)-methylbenzylcarbamate] | 20 | Chiralpak ® AS-V | No | n.a. | n.a. |
| Coated | cellulose tris(3,5-dimethylphenylcarbamate) | 20 | Lux Cellulose 1 | No | n.a. | n.a. |
| Coated | cellulose tris(3-chloro-4-methylphenylcarbamate) | 20 | Lux Cellulose 2 | No | n.a. | n.a. |
| Coated | Cellulose tris(4-methylbenzoate) | 20 | Lux Cellulose 3 | No | n.a. | n.a. |
| Coated | cellulose tris(4-chloro-3-methylphenylcarbamate) | 20 | Lux Cellulose 4 | No | n.a. | n.a. |
| Coated | amylose tris(5-chloro-2-methylphenylcarbamate) | 20 | Chiralpak ® AY | Yes | 1.3 | Almost |
| Coated | amylose tris(3,5-dimethylphenylcarbamate) | 10 | Lux-Amylose-1 | Yes | 1.3 | Almost |
| Coated | amylose tris(3-chloro-4-methylphenylcarbamate) | 20 | Chiralpak ® AZ | Yes | 2.7 | Yes |

Example 2 Chiral Stationary Phases Screening

The ability of a set of chiral stationary phases to separate ethyl 3-amino-1-[(3R,4S)-4-cyanotetrahydropyran-3-yl] pyrazole-4-carboxylate (Formula VI) from a racemic mixture of ethyl 3-amino-1-[(3R,4S)-4-cyanotetrahydropyran-3-yl]pyrazole-4-carboxylate and ethyl 3-amino-1-[(3S,4R)-4-cyanotetrahydropyran-3-yl]pyrazole-4-carboxylate (Formula V) was determined using acetonitrile as solvent for diluting the samples and as eluent (or mobile phase) for performing the chromatography. The results are given in Table 2.

The operating conditions for this study are given in Table 2 below,

As attested by the results presented in Table 3, less than half of the chiral stationary phases investigated allowed for some degree of separation of the racemic mixture of (V). Among those enabling the separation of (V) only two columns allowed baseline resolution of (V): amylose tris(3-chloro-5-methylphenylcarbamate) immobilized on silica gel column (Chiralpak® IG) and amylose tris(3-chloro-4-methylphenylcarbamate) coated on silica gel column (Chiralpak® AZ).

Example 3—Productivity

A 20 mg of the racemic mixture (V) was solubilized at 200 g/L in acetonitrile. This solution was injected on an amylose tris(3-chloro-5-methylphenylcarbamate) immobilized on silica gel column (Chiralpak® IG) (250×4.6 mm). The sample was eluted with acetonitrile at 25° C. Both enantiomers were obtained. The productivity (KKD) was estimated to be between 3.0 and 3.5 kg of racemate/kg of chiral stationary phase/day.

A 20 mg of the racemic mixture (V) solubilized at 200 g/L in acetonitrile was also injected on amylose tris(3-chloro-4-methylphenylcarbamate) coated on silicon gel column (Chiralpak® AZ) (250×4.6 mm). After elution with acetonitrile at 25° C., both enantiomers were obtained. The productivity (KKD) was estimated to be between 4.0 and 5.0 kg of racemate/kg of chiral stationary phase/day.

The invention claimed is:

1. A process of producing a compound of Formula VI

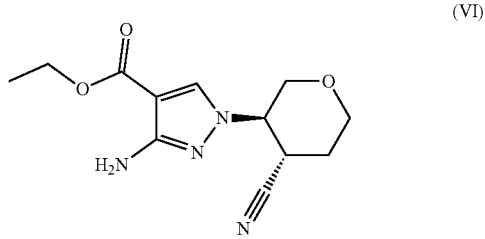 [SMILES: CCOC(=O)c1cn([C@H]2COCC[C@@H]2C#N)nc1N]

(VI)

from a mixture of enantiomers comprising separating the enantiomers of a racemic mixture of Formula V

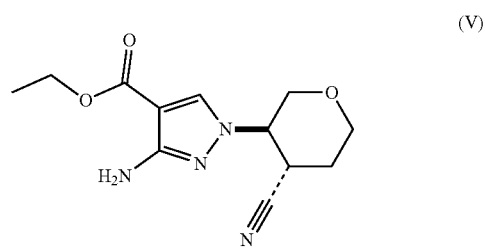 [SMILES: CCOC(=O)c1cn([C@H]2COCC[C@@H]2C#N)nc1N]

(V)

by chiral chromatography using an eluent and a chiral stationary phase selected from amylose tris(3-chloro-4-methylphenylcarbamate) and amylose tris(3-chloro-5-methylphenylcarbamate) wherein the eluent is acetonitrile.

2. The process of claim 1, wherein productivity of the process is greater than 2.0 KKD.

3. The process of claim 1, wherein the chiral stationary phase is amylose tris(3-chloro-5-methylphenylcarbamate) immobilized on silica gel.

4. The process of claim 1, wherein the chiral stationary phase is amylose tris(3-chloro-4-methylphenylcarbamate) coated on silica gel.

5. The process of claim 1, wherein the productivity of the process is in the range of about 2.0 to about 6.0 KKD.

6. The process of claim 1, wherein the selectivity of the process is the range of about 1.0 to about 4.0.

7. The process of claim 1, wherein the process is conducted at a temperature between about 20° C. to about 40° C.

8. The process of claim 1, wherein the process has a concentration of the racemic mixture (V) from about 100 g/L to about 300 g/L.

9. A method of isolating ethyl 3-amino-1-[(3R,4S)-4-cyanotetrahydropyran-3-yl]pyrazole-4-carboxylate (VI), substantially free of ethyl 3-amino-1-[(3S,4R)-4-cyanotetrahydropyran-3-yl]pyrazole-4-carboxylate, said method comprising
a) absorbing a racemic mixture of ethyl 3-amino-1-[(3R,4S)-4-cyanotetrahydropyran-3-yl]pyrazole-4-carboxylate and ethyl 3-amino-1-[(3S,4R)-4-cyanotetrahydropyran-3-yl]pyrazole-4-carboxylate (V) onto a chiral separation medium;
b) passing a solvent system through the chiral separation medium in an amount sufficient to elute ethyl 3-amino-1-[4-cyanotetrahydropyran-3-yl]pyrazole-4-carboxylate enantiomers from the separation medium;
c) isolating ethyl 3-amino-1-[(3R,4S)-4-cyanotetrahydropyran-3-yl]pyrazole-4-carboxylate (VI), substantially free of ethyl 3-amino-1-[(3S,4R)-4-cyanotetrahydropyran-3-yl]pyrazole-4-carboxylate;
wherein said chiral separation medium is amylose tris(3-chloro-5-methylphenylcarbamate) immobilized on silica gel or
amylose tris(3-chloro-4-methylphenylcarbamate) coated on silica gel.

10. The method of claim 9, wherein the chiral separation medium is amylose tris(3-chloro-5-methylphenylcarbamate) immobilized on silica gel.

11. The method of claim 9, wherein the chiral separation medium is amylose tris(3-chloro-4-methylphenylcarbamate) coated on silica gel.

12. The method of claim 9, wherein the solvent system comprises is acetonitrile.

13. The method of claim 9, wherein the process has a productivity of in the range of about 2.0 to about 6.0 KKD.

14. The method of claim 9, wherein the selectivity of the process is the range of about 1.0 to about 4.0.

15. The method of claim 9, wherein the temperature is between about 20° C. to about 40° C.

16. The method of claim 9, wherein the concentration of the racemic mixture (V) is about 100 g/L to about 300 g/L.

17. The method of claim 5, wherein the productivity of the process is in the range of about 3.0 to about 5.0 KKD.

18. The method of claim 6, wherein the selectivity of the process is the range of about 1.5 to about 3.5.

19. The method of claim 7, wherein the process is conducted at a temperature between about 25° C. to about 35° C.

20. The method of claim 8, wherein the process has a concentration of the racemic mixture (V) of about 200 g/L.

* * * * *

UNITED STATES PATENT AND TRADEMARK OFFICE
CERTIFICATE OF CORRECTION

PATENT NO. : 12,281,104 B2
APPLICATION NO. : 17/606248
DATED : April 22, 2025
INVENTOR(S) : Christophe Pierre Alain Chassaing and Karl-Heinz Grimm Page 1 of 1

It is certified that error appears in the above-identified patent and that said Letters Patent is hereby corrected as shown below:

In the Claims

Column 12, Lines 35-36 Claim 12 reads:
"12. The method of claim 9, wherein the solvent system comprises is acetonitrile."
Should be corrected to read:
--12. The method of claim 9, wherein the solvent system is acetonitrile.--

Signed and Sealed this
Twenty-seventh Day of May, 2025

Coke Morgan Stewart
*Acting Director of the United States Patent and Trademark Office*